United States Patent [19]

Duggan

[11] Patent Number: 4,481,950
[45] Date of Patent: Nov. 13, 1984

[54] ACOUSTIC SIGNALLING APPARATUS FOR IMPLANTABLE DEVICES

[75] Inventor: Stephen R. Duggan, Rosemount, Minn.

[73] Assignee: Medtronic, Inc., Minneapolis, Minn.

[21] Appl. No.: 250,539

[22] Filed: Apr. 3, 1981

Related U.S. Application Data

[63] Continuation of Ser. No. 33,998, Apr. 27, 1979, abandoned.

[51] Int. Cl.³ .................................................. A61N 1/36
[52] U.S. Cl. ............................................. 128/419 PT
[58] Field of Search ....... 128/419 P, 419 PG, 419 PS, 128/419 PT, 419 R

[56] References Cited

U.S. PATENT DOCUMENTS

3,693,627  9/1972  Berkovits .................... 128/419 PG
4,041,954  8/1977  Ohara .......................... 128/419 PT
4,102,346  7/1978  Fulker ......................... 128/419 PS

*Primary Examiner*—William E. Kamm
*Attorney, Agent, or Firm*—Merchant, Gould, Smith, Edell, Welter & Schmidt

[57] ABSTRACT

Acoustic signalling apparatus is provided for use with implantable devices for therapeutic, diagnostic or other medical or scientific purposes, for implantation in living animal bodies, including human bodies. A piezoelectric element positioned adjacent the inside wall of the implantable device is selectively energized by an oscillator circuit operating from an energy storage capacitor. Switching devices are provided for activating the acoustic signal according to sensed medical conditions within the body, or according to operating conditions of the device itself, such as indicating approaching end of battery life.

14 Claims, 7 Drawing Figures

ACOUSTIC SIGNALLING APPARATUS FOR IMPLANTABLE DEVICES

This is a continuation of now abandoned application Ser. No. 033,998, filed Apr. 27, 1979, entitled "Acoustic Signalling Apparatus for Implantable Devices".

TECHNICAL FIELD OF THE INVENTION

The invention pertains to the field of devices for implantation in living animals, including human bodies, for therapeutic, diagnostic or other medical or scientific purposes, including, but not limited to heart pacemakers. More particularly, the invention pertains to apparatus for providing acoustic signals which may be transmitted from within the implanted device for reception outside the body.

BACKGROUND OF THE PRIOR ART

Great progress has been made in the field of implantable devices for medical or biological purposes. By far the most common types of implantable devices are the heart pacemakers, but other types of implantable devices have been developed or proposed also, including sensing devices for measuring various medical conditions within the body, metered drug administering devices, muscle stimulators and nerve stimulators. With the great strides that have been made in miniaturization of electronic circuit components, it is possible to provide increasingly sophisticated and varied control and monitoring functions within an implantable device. These advances have made it important to provide an efficient means for transmitting data from within the implanted device to be received and sensed outside the body. The data to be thus transmitted can represent diagnostic data concerning sensed medical conditions within the body, or it can represent data indicative of the operating condition of the circuits within the implanted device itself. One example of this latter category of data can be the important function of transmitting signals indicative of the amount of life remaining in the battery or other power source which powers the implanted device.

It has been proposed previously to use sound or ultrasound waves for transmitting signals from a device implanted within the body. One prior art example is proposed in U.S. Pat. No. 3,672,352 to Summers, which discloses in general form an implantable device having a sensor and a signalling device. A number of different methods for signalling are suggested, including an audible signal. Another system is proposed in U.S. Pat. No. 4,041,954 to O'Hara, which also discloses sensors and various types of energy signal transmitting means, including sound or ultrasonic waves. It is recognized in the prior art that energy from the battery or other energy source for the implanted device must be conserved for long life, and that energy usage by the transmitting means must be kept to a minimum. Accordingly, both of the abovementioned prior art references suggest the use of circuits requiring external microphones for picking up the weak sound signals generated. To further conserve energy they suggest means for supplying energy externally of the body to within the implanted device, or means for inhibiting the implanted signal transmission means until activated externally by a magnet, pressure switch, etc. The weak acoustic signals thus provided by the prior art patents mentioned above, together with the microphones and possible external energization or activation means limit their applicability to testing under controlled conditions, as in a laboratory, hospital, or a doctor's office.

In contrast, the present invention provides audible signalling means for an implanted device which, while operating with very low drain on the energy source of the implanted device, provides an audible signal which may be heard externally of the body with the unaided ear. This feature makes it very useful for classes of devices intended for implantation in human patients, and where a warning must be given to the patient in case of problems associated with a medical process or condition being monitored or treated. For example, the alert signal can be used with a device for measuring blood pressure, in which case the alert signal would prompt the user to take corrective action, such as taking medication or calling his physician. The invention can similarly be used with any physiologically measurable parameters of interest.

As mentioned above, the invention is especially well adapted to providing a warning to the patient when the battery or other energy source in an implantable pacemaker approaches the end of its life. Because of the obvious undesirability and risk to the patient's health should failure of the energy source for a pacemaker occur, a great deal of effort has been expended in prolonging the life of pacemaker batteries, and also in solving the problem of deciding when to replace them. Since replacement involves a surgical procedure, even though not a major one, it is obviously desirable to avoid unnecesary replacement. However, since the useful life of the battery depends upon many variables such as the duty cycle of the device, it is difficult or impossible to predict. Thus, the solution of periodic replacement of the battery with an interval being determined to avoid a predetermined risk of battery failure results in unnecessarily frequent replacement in the vast majority of cases. A method for indicating approaching battery depletion is described in U.S. Pat. No. 3,842,844, wherein circuitry is provided for increasing the pulse width of the output signals, and decreasing the pulse repetition rate, as the battery becomes depleted. Observation of the pulse width and repetition rate, as compared with the known voltage properties of an aging battery, can serve as an indication of the time to replace a pacemaker. However, it cannot be assumed that the patient will necessarily become aware of these indications, and practical reliability may therefore depend upon measurement of these parameters in the context of the doctor's office, a variable beyond the control of the device manufacturer.

Other methods, as disclosed in U.S. Pat. No. 3,618,615 and U.S. Pat. No. 3,713,449 have been proposed which allow an attending physician to observe the response to certain pulse parameters to determine battery life. In general, these methods have the disadvantages of requiring interrogation of the unit by a magnetically operated switch and instruments to read operating parameters. These systems are therefore dependent upon a physician to make the determination, and they will not pick up premature battery failures under normal sampling plans.

Other systems proposed in U.S. Pat. No. 3,783,877 use an auxiliary battery in the implanted device and a switching network that brings it into use when the voltage in the primary battery drops to a predetermined level. Either a variation in the pulse rate or the provision of an additional set of electrodes remote from the heart are provided to indicate switchover to the secondary battery. This system has the disadvantage of requiring two separate batteries where space is at a premium within the pacemaker. Further, the provision of a second set of electrodes provides another complexity that is not justified in all cases.

SUMMARY OF THE INVENTION

To overcome these and other problems, the present invention provides an acoustic signalling apparatus for a device intended to be implantable in an animal or human body for transmitting signals indicative of sensed conditions within either the body or the implantable device itself, to be received outside the body. The apparatus includes a transducer for generating acoustic signals in response to applied electrical signals, an oscillator circuit operable when energized to apply electrical signals to the transducer, and means for selectively energizing the oscillator in response to sensed conditions within the body or implantable device. This may include energy storage means, means for applying quantities of energy to the energy storage means from the battery or other energy source of the implantable device, and means for connecting the energy storage means to the oscillator circuit, for causing the transducer to emit corresponding pulses of acoustic energy for detection outside the body.

According to another aspect of the invention, an acoustic end-of-battery life signalling device is provided for an implantable pacemaker. A transducer is mounted in the pacemaker adjacent the housing, and an oscillator circuit, when energized, applies electrical signals to the transducer. The oscillator circuit receives energy from an energy storage capacitor, which is selectively connected by switching means to receive a charge from the battery of the pacemaker on a periodic basis, for example, simultaneous to the pulse generation interval of the pacemaker. A battery end-of-life detector senses a drop in the output of the pacemaker battery to a predetermined level, and activates a switching means for selectively connecting the energy storage capacitor to the oscillator so as to enable the acoustic alert apparatus to transmit acoustic pulses warning of the end of the battery life.

DETAILED DESCRIPTION OF THE PREFERRED EMBODIMENTS

Figure 1:
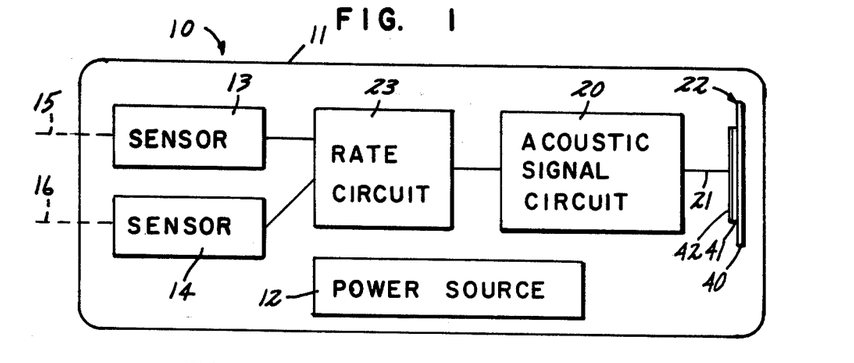
FIG. 1 is a schematic block diagram of an implantable sensing device using the acoustic signalling apparatus of the present invention.

Referring to FIG. 1, reference number 10 generally designates an implantable sensing and signalling device, which includes a housing 11 and a power source 12. Also included are a plurality of sensors, of which two are shown indicated by reference numbers 13 and 14, although it will be appreciated that any number of sensors could be provided according to the design purpose of the device. These sensors may be designed to monitor given biological parameters, and for this purpose they may require electrical leads indicated by broken lines 15 and 16 which would extend through the wall of housing 11 by way of suitable insulating and sealing means, to a location within the body appropriate to the parameter being sensed.

Device 10 also includes an acoustic signalling circuit 20 according to the present invention. Circuit 20 connects via conductor 21 to transducer 22. As is described more fully below, circuit 20 includes an oscillating circuit operative when energized to apply signals to transducer 22, causing it to emit acoustic signals to be received externally of the body in which the device is implanted. For purposes of power economy, the acoustic signalling circuit is designed to operate in a pulse rather than continuous mode, and the pulse repetition can be controlled or modulated as to number, duration and spacing to transmit data. For example, a rate circuit 23 is indicated in FIG. 1, and it may be designed as is generally known to provide output pulses having a repetition rate which is a function of the condition of the signals being generated by one or more of the sensors 13, 14, so that the data being sent corresponds to the sensed conditions. The power source 12 of course is connected to the other circuits as required, although the connections have been deleted from FIG. 1 for purposes of clarity.

Figure 2:
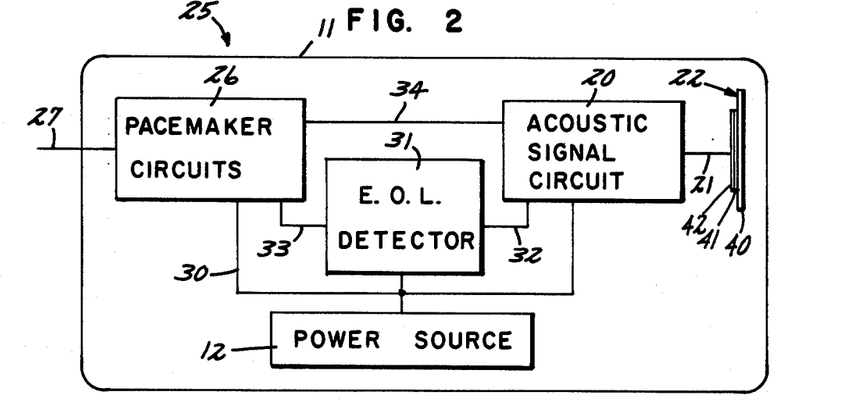
FIG. 2 is a schematic block diagram of an implantable heart pacemaker using the acoustic signalling apparatus of the present invention.

In FIG. 2, there is shown in block diagram form an implantable pacemaker generally indicated by reference number 25. It includes an hermetically sealed housing, indicated by reference number 11, as is generally known in the art, for housing the devices and components of the pacemaker. Reference number 26 generally designates the pacemaker circuits, which perform the function of generating the cardiac stimulating pulses, and delivering them via one or more leads which pass through the wall of housing 11 by means of suitable insulating and sealing means as is generally known, for conducting the pulses to the heart. One such lead is indicated in FIG. 2 by reference number 27. Any type of pacemaker circuitry can be used for block 26 in conjunction with the present invention, including, but not limited to, asynchronous, demand, and sequential pacemakers and the like.

Power source 12, which usually takes the form of a battery, connects via a power conductor 30 to the pacemaker circuits, and also to an end-of-life detector 31 and the acoustic signalling circuit 20. End-of-life detector 31 includes circuitry for detecting a drop in the output of power source 12 below a predetermined value, indicating the approach of the end of the useful life of the power source. Detector 31 connects by a control conductor 32 to control the energization of acoustic signalling circuit 20 to cause it to emit an alert or warning signalling indicating approaching end-of-life of the power source. Detector 31 may also connect via a conductor 33 to the pacemaker circuits 26 for use in lengthening the pulse width and slowing the pulse repetition rate in the manner of the prior art discussed above as a further indication of approaching end of battery life, since the acoustic signalling technique is preferably used in conjunction with existing techniques for indicating end of battery life. Another conductor indicated by reference number 34 connects from the pacemaker circuits 26 to acoustic signalling circuit 20. As is explained more fully below with reference to FIG. 7, the output pulses of the pacemaker, or the oscillator reset pulses in the case of a demand-type pacemaker, can be used as timing signals for establishing the repetition rate of the acoustic warning signals in the event of approaching end of battery life, and conductor 34 conveys the control signals for this purpose.

Figure 3:
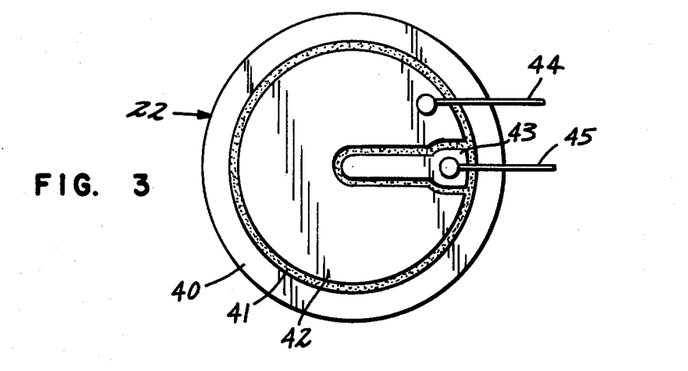
FIG. 3 is an enlarged view in top plan of a piezoelectric transducer for use in the preferred embodiment of the invention.
Figure 4:
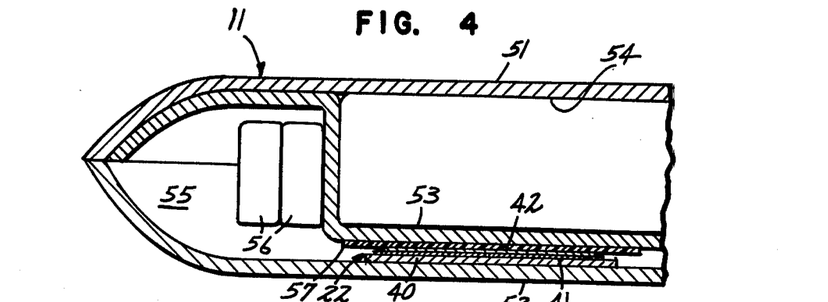
FIG. 4 is an enlarged sectional view in side elevation of an implantable pacemaker showing mounting of the transducer of FIG. 3 in the preferred embodiment.

Referring now to FIGS. 3 and 4, the transducer used in the preferred embodiment of the invention, and its mounting in a pacemaker housing are shown. The preferred transducer as shown in FIG. 3 is a ceramic piezoelectric element. It comprises a generally circular brass disc or plate 40, on top of which is bonded a ceramic piezoelectric element indicated by reference number 41. Brass disc 40 serves as one electrode for the transducer, and a metalized layer is formed on top of piezoelectric element 41 to serve as the other electrode. In FIG. 3, the metalized layer electrode is indicated by reference number 42. A zone of layer 42 is cut away to provide separation for a separate tab or finger portion indicated by reference number 43. This tab is also made of the metalized electrode layer in contact with the underlying ceramic piezoelectric element, but it is electrically separate from electrode portion 42, so as to provide a feedback electrode. Electrical connections are made via brass disc 40, and an electrical conductor 44 which is soldered to electrode 42, and conductor 45 which is soldered to electrode 43.

Piezoelectric transducers of this type are commercially available, and in the preferred embodiment a transducer number 70046 of Linden Laboratories, State College, Pa. is used.

FIG. 4 shows a mounting technique for mounting the transducer of FIG. 3 in the housing of an implantable pacemaker. The housing of FIG. 4 is generally of the type shown in U.S. Pat. No. 3,957,056 issued May 18, 1976 to Comben et al., although other types of housings as are generally known can be used also. Housing 11 generally has an upper wall 51 and a lower wall 52 which are joined together and welded around the circumference of the device to form the hermetically sealed housing. An inner partition 53 is provided to form a battery compartment 54, and a space 55 for mounting of the various circuit devices 56.

Transducer 22 is mounted to the inside of lower wall 52. Specifically, brass disc 40 may be secured to wall 52 by a suitable adhesive, or by welding. Adhesive bonding can be accomplished by coating the entire surface of the disc with Eastman 910 adhesive, for example. A plastic insulating layer 57 is sandwiched between the top of transducer 22 and inner partition 53 for purposes of electrical insulation. In case a separate inner partition 53 is not used, plastic layer 57 would insulate the transducer from the battery case itself.

Figure 5:
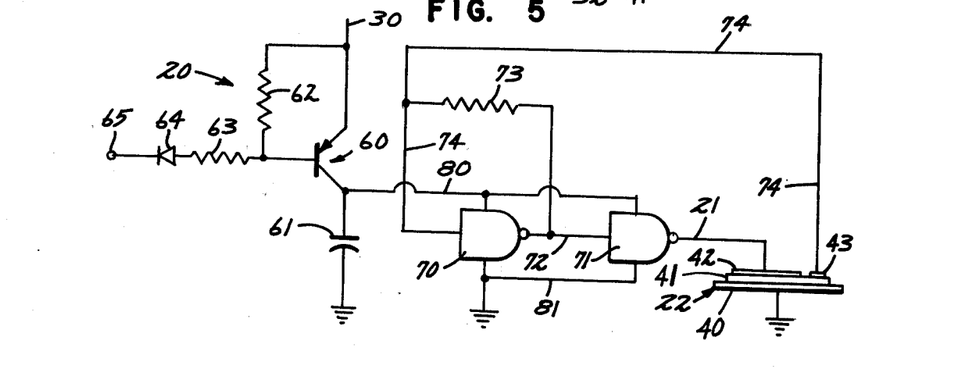
FIG. 5 is a schematic diagram of the circuit for the acoustic signalling apparatus according to the preferred embodiment of the invention.

Referring now to FIG. 5, acoustic signalling circuit 20 and transducer 22 are shown in detail. A switching PNP transistor 60 has its emitter connected to conductor 30 which connects to the battery or other power source for the implanted device. A capacitor 61 connects between the collector of transistor 60 and signal ground. The base of transistor 60 connects to a pair of resistors 62 and 63. The other side of resistor 62 connects to power conductor 30, and the other side of resistor 63 connects to the anode of a diode 64. The cathode of this diode serves as the input terminal, indicated by reference number 65.

The oscillator circuit is provided by a pair of CMOS inverters, together with a linearizing resistor and the feedback electrode of the transducer. Inverter 70 has its input connected to conductor 74 and its output connected via conductor 72 to linearizing resistor 73, whose other terminal connects to conductor 74. The function of resistor 73 is to force inverter 70 into linear operation. Conductor 72 also connects to the input to inverter 71. The output of inverter 71 connects via conductor 21 to electrode 42 of transducer 22. Feedback electrode 43 connects to a branch of conductor 74. The remaining terminal, brass disc 40 of transducer 22, is connected to signal ground.

Operating power for inverters 70 and 71 is provided by conductors 80 and 81. Conductor 81 connects the appropriate ground terminals of inverters 70 and 71 to signal ground, although this connection can be switched as it is in the embodiment of FIG. 7 described below. Conductor 80 connects the positive power supply terminals of inverters 70 and 71 to capacitor 61.

Figure 6:
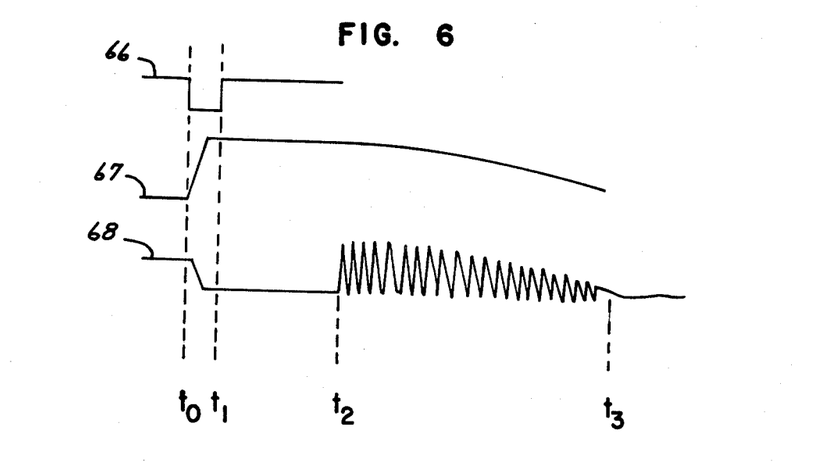
FIG. 6 is a graph showing pertinent waveforms illustrating the operation of the circuit of FIG. 5.

The operation of the circuit of FIG. 5 is explained with reference to the waveforms of FIG. 6. The circuit is designed to operate in response to a pulse input at terminal 65, as indicated by waveform 66. This waveform, which goes negative at time $t_0$ and lasts until $t_1$, establishes conduction through the base of transistor 60, thus turning it on and establishing a charging current through transistor 60 to capacitor 61. Resistor 63 serves to limit base current for transistor 60 and diode 64 is provided for isolation of the circuit from other circuits connected to input 65, for example in the case of multiple input devices. Resistor 62 is provided for temperature stability and compensation for transistor 60 as is generally known.

The triggering pulse for charging capacitor 61 can be rather narrow and of low energy, for example on the order of 500 to 1,000 microseconds in width. As described above, it serves to transfer a fixed quantity of energy from the power source of the implanted device to capacitor 61, which then stores the energy for use by the oscillating circuit which converts it into acoustic energy. The voltage at capacitor 61 is indicated by waveform 67.

Prior to the charging of capacitor 61, inverters 70 and 71 are not active since they have no other connection to a source of power. After capacitor 61 receives its charge, the oscillating circuit breaks into oscillation, following a delay while the capacitance of the piezoelectric element is being charged, as indicated by waveform 68 of FIG. 6 at time $t_2$. With inverter 70 operating as an amplifier, and with the cascade connection of inverters 70 and 71 providing 360 degrees of phase shift, the circuit oscillates as determined by the resonant frequency of the piezoelectric element. The fact that the frequency of the oscillator is determined by the resonant frequency of the piezoelectric element is advantageous in terms of efficient conversion of the energy stored on capacitor 61 into acoustic energy. This factor automatically compensates for variations in piezoelectric elements and mounting thereof, so that operation always occurs at the optimum efficiency frequency. A voltage applied to conductor 21 causes a mechanical displacement of the piezoelectric element which in turn generates a feedback voltage at electrode 43, which is fed back into the input of the amplifier. The resulting phase shift will sustain oscillations, with the vibrations of the transducer element providing the desired tone for as long as sufficient power is supplied to inverters 70 and 71 by capacitor 61. After time $t_2$ in FIG. 6, the voltage at capacitor 61 gradually decays as the power is being converted into acoustic energy, and the amplitude of the oscillation correspondingly decreases, until there is insufficient voltage left to operate, and oscillations cease, as indicated at time $t_3$. The net effect is the production of a burst or pulse of acoustic energy having a frequency determined by the resonant frequency of the mounted transducer, typically 1,000 to 3,000 kilohertz for audible uses, and having a duration determined by the amount of energy stored in capacitor 61. In the preferred embodiment, the pulse or tone duration is approximately 80 milliseconds. The repetition rate of course is dependent upon the repetition rate of the pulses applied to terminal 65. Of course if a steady state low signal were to be applied to terminal 65 so as to keep transistor 60 in conduction, power would continue to be applied to conductor 80 and the generated tone would be continuous. However, this mode of operation may not be preferred because of the relatively larger amount of power consumption that it would involve.

Figure 7:
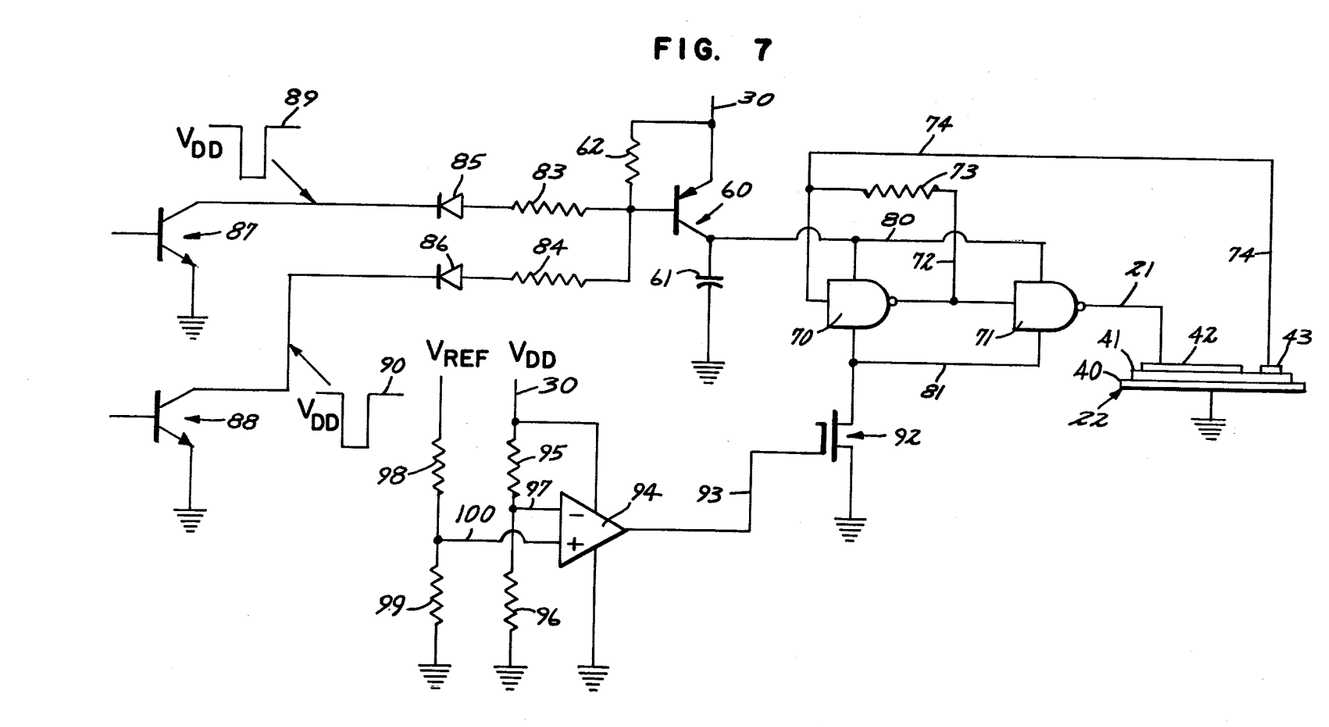
FIG. 7 is a schematic diagram of the preferred embodiment of the present invention for signalling end-of-battery life for an implantable pacemaker.

FIG. 7 shows a preferred embodiment of the invention based on the circuit of FIG. 5, but adapted for use as an end of battery life signalling means for an implantable heart pacemaker.

In FIG. 7, the basic circuitry of FIG. 5 has been supplemented with additional circuits for interfacing with the circuits of an implantable heart pacemaker to provide an audible alerting signal indicating approaching end of battery life. The basic circuit including transistor 60, capacitor 61, inverters 70 and 71, transducer 22 and associated components is the same as previously described in FIG. 5, and these components are numbered the same in FIG. 7. Instead of a single input to the base of transistor 60, a pair of resistors 83 and 84 are connected to the base of transistor 60 and to resistor 62. The anode of a diode 85 is connected to resistor 83, and the cathode thereof connects to the collector of a transistor 87, the emitter of which is connected to signal ground. In similar fashion, diode 86 connects from resistor 84 to the collector of a transistor 88. Transistor 87 represents the NPN pacemaker output stage, and its connection to the acoustic signalling circuit as shown results in providing a negative going pace pulse as indicated by reference number 89 with each pacemaker stimulating output pulse. The pacing pulse at the collector of transistor 87 drops essentially from the battery supply voltage to close to signal ground for a duration of 100 to 2,000 microseconds, and this pulse turns on transistor 60 to charge capacitor 61 as described previously.

In case of a demand-type pacemaker, transistor 88 represents the NPN pacemaker sense amplifier oscillator reset output, and it also presents a negative going output pulse as indicated by reference number 90. This pulse also serves to turn on transistor 60 and charge capacitor 61. With the connections thus shown, transistor 60 will be turned on to charged capacitor 61 with every heartbeat, either spontaneous or stimulated. If the pacemaker puts out an output pulse to stimulate the heart of the patient, transistor 87 will provide the turn-on for transistor 60, and if a spontaneous beat occurs, the detection and reset circuit in the demand-type pacemaker will cause transistor 88 to provide the pulse for turning on transistor 60. Thus, transistor 60 will be energized to charge capacitor 61 at a repetition rate of roughly 72 times per minute, or at whatever other rate the pacemaker is set to pace at, or at which the heart is pacing itself.

Although a continually repeating charging path is provided for capacitor 61 in FIG. 7, no discharge thereof will actually be taking place unless the circuit from conductor 81 to signal ground is completed. This path is controlled by a switching device, which in the preferred embodiment is an N-type FET 92. One terminal of FET 92 connects to conductor 81, another to signal ground, and the gate terminal connects to conductor 93, from the output of voltage comparator 94. The power and ground connections necessary for operating integrated circuit voltage comparator 94 are connected to power conductor 30, from the pacemaker battery or other power supply and to signal ground respectively.

Comparator 94 is a low power integrated circuit operational amplifier operated open loop as a voltage comparator. Voltage references are applied to the inverting and non-inverting inputs thereof by resistor networks as follows. A voltage divider comprising resistors 95 and 96 connects from power conductor 30 to signal ground, with the junction point 97 connecting to the inverting input of the comparator. A voltage divider comprising resistors 98 and 99 connects from a voltage reference source $V_{REF}$ to signal ground with the junction point 100 of the resistors connecting to the non-inverting input of the comparator.

Voltage reference $V_{REF}$ is chosen to provide a stable reference voltage somewhat less than the battery or power supply voltage $V_{DD}$ and this reference, in connection with the value selection for the two voltage divider resistor networks causes comparator 94 to change its output state when the voltage at conductor 30 drops below a predetermined value, indicating approaching end of useful battery life. The actual value chosen depends upon the characteristics for the type of battery to be used. As an example, the $V_{REF}$ source can be a current source driving a resistor.

It is desirable that the acoustic alerting function provided herein for end of battery life be combined with the conventional circuitry for pulse duration and rate modification indicating the same thing, so it is convenient that device 92 be connected to operate in conjunction with the sensing means for the prior types of end-of-life circuits mentioned above.

In operation, even though capacitor 61 is continually being charged, no oscillation will take place through the oscillator circuit until transistor FET switch 92 is turned on, completing the path to ground from conductor 81. Thus, as long as the supply battery voltage remains above the predetermined level, transistor 92 remains off, and no power at all is consumed in the audio signalling circuitry.

As soon as the predetermined voltage is reached and switch 92 is turned on, the oscillator circuit will operate as described above with reference to FIG. 5, to produce a tone burst from transducer 22, lasting approximately 80 milliseconds in the preferred embodiment. Somewhat less than a second later, at the next paced or spontaneous heartbeat, capacitor 61 is recharged and another tone burst is produced. The effect is to produce a constant "beeping" signal which can be heard by the patient or others. The amount of energy expanded on each beep or tone burst is determined by the amount stored in capacitor 61, and is essentially independent of the triggering pulse duration or other factors concerning operation of the other pacemaker circuits.

The presently preferred circuit uses the following component values:

| List of Component Values | |
|---|---|
| Diode 85 | FDH 666 |
| Diode 86 | FDH 666 |
| Resistor 62 | 1 Megohm |
| Resistor 73 | 20 Megohms |
| Capacitor 61 | 5.6 Microfarad |
| Gates 70, 71 | CD 4049 |
| Transistor 60 | 2N 2907 |
| Transducer | Linden Labs 70065 |

A device built according to the above values has a very low current drain, on the order of 3 microamperes. A hermetically sealed device incorporating the circuit described above was implanted in a canine. Sound level tests were performed with an audiometer placed 2 inches from the implanted device as follows:

|  | Reading | Ambient Noise |
|---|---|---|
| Pre Implant: | 47 db | 35 db |
| Immediate After Implant: | 37 db | 35 db |
| One Week Post Implant: | 40 db | 20 db |
| Two Week Post Implant: | 39 db | 20 db |

Several observers were able to hear the "beeper" 6 to 8 feet from the animal. This hearing distance is in close agreement theoretical distances assuming a 21 db signal over essentially random noise 2 inches from the device.

The present invention thus provides a highly effective and energy efficient acoustic signalling means for an implantable device, for providing signals which are audibly detectable outside the body by the unaided ear. By suitable interfacing circuits, the acoustic signals can represent important medical diagnostic parameters from within the body, or operating conditions, such as end of battery life or the like, concerning the operation of the implanted device itself.

What is claimed:

1. Acoustic end of battery life signalling apparatus for an implantable pacemaker which has a battery and a housing, comprising:
   (a) a transducer for generating acoustic signals in response to applied electrical signals;
   (b) means mounting said transducer in said pacemaker adjacent the housing of the pacemaker;
   (c) an oscillator circuit operable when energized to apply electrical signals to the transducer;
   (d) an energy storage capacitor;
   (e) first switching means connected for selectively charging the energy storage capacitor from the battery of the pacemaker, said switching means connected for switching on in response to pulses from an output of the stimulating pulse generating circuit of the pacemaker;
   (f) battery end-of-life detection means for producing a signal in response to a drop in the output of the pacemaker battery to a predetermined level;
   (g) further switching means selectively connecting said energy storage capacitor to said oscillator circuit, and means connecting said further switching means for control by the signal produced by the end-of-life detector, whereby the acoustic signalling apparatus is enabled to transmit acoustic pulses warning of the end of battery life.

2. Acoustic signalling apparatus according to claim 1 for a demand-type pacemaker which includes a sense amplifier providing reset pulses for resetting the output pulse generating circuits of the pacemaker, further including means connecting said reset pulses to said first switching means for activation by either a pacemaker output pulse or a reset pulse.

3. Acoustic signalling apparatus according to claim 10 wherein said first switching means comprises a transistor connected for selectively conducting current from the battery of the pacemaker to said energy storage capacitor, and having its base connected for switching by either a pacemaker output pulse or a sense amplifier reset pulse.

4. Acoustic signalling apparatus according to claim 1 wherein said transducer comprises a piezoelectric element, and including means for mounting the element to the inside wall of the housing for the implantable pacemaker.

5. Acoustic signalling apparatus according to claim 4 wherein said piezoelectric element includes a pair of electrodes connecting from the oscillator circuit for energization thereof and a feedback electrode, and further including conductor means connecting the feedback electrode to the input of the oscillator circuit.

6. Acoustic signalling apparatus according to claim 1 wherein said first switching means comprises a transistor connected for conducting current from the battery to the energy storage capacitor, and having its base electrode connected for switching in response to pulses from an output of the stimulating pulse generating circuit of the pacemaker.

7. Acoustic signalling apparatus according to claim 1 wherein said battery end-of-life detection means comprises means for establishing a reference voltage, means for comparing the voltage of the pacemaker battery to the reference voltage and for producing said signal in response to a drop in the output of the pacemaker battery to a predetermined level, and means for connecting said comparing means for control of said further switching means.

8. Acoustic signalling apparatus for a device that includes a housing and that is implantable in an animal body for transmitting signals to be received outside the body comprising:
   (a) a piezoelectric transducer element having a pair of electrodes for energization and a third feedback electrode;
   (b) means for mounting said piezoelectric element inside the implantable device adjacent a wall of the housing thereof;
   (c) an oscillator circuit comprising a cascade connected pair of CMOS inverters, a linearizing resistor connected thereto, and a feedback conductor connected from the feedback electrode to the input of the oscillator, and means connecting the output of the oscillator to the energization electrodes of the piezoelectric element; and
   (d) means for applying emergization current to said oscillator circuit to thereby cause the transducer to emit an acoustic signal.

9. Acoustic signalling apparatus according to claim 8 wherein said means for energizing said oscillator comprises a capacitor and means for selectively charging said capacitor to provide acoustic output pulses.

10. Acoustic signalling apparatus according to claim 8 wherein said means for energizing said oscillator comprises a capacitor, first switching means for selectively charging said capacitor, and first switching means for selectively connecting said capacitor to said oscillator circuit, so that the operation and repetition of the acoustic signalling apparatus can be controlled.

11. A low power consumption pulsed acoustic signalling apparatus, to be used with an implantable device having an energy source, for transmitting acoustic signals audible to the unaided ear outside the body in which the device is implantable, comprising:
 (a) a transducer for generating acoustic signals in response to applied electrical signals;
 (b) oscillator circuit means operable when energized to apply electrical signals to said transducer;
 (c) energy storage means connected to said oscillator circuit means, for providing energy to be used for energizing said oscillator circuit means, said energy storage means holding a relatively minute quantity of energy when fully charged as compared to said energy source;
 (d) switching means for selectively applying energy from the energy source to charge said energy storage means; and
 (e) means responsive to sensed conditions within the body for activating said switching means to recurrently charge said energy storage means so that between charges said energy storage means delivers a decaying pulse of energy to said oscillator circuit means which in turn applies said electrical signals to said transducer to cause said transducer to emit corresponding pulses of acoustic energy audible outside the body by the unaided ear, said pulses having a duration corresponding to the discharge period of said energy storage means and having an acoustic energy limited by the energy available from said energy storage means wherein relatively smaller quantities of power are utilized to signal as compared to energizing said oscillator circuit and transducer directly from said energy source.

12. A low power consumption pulsed acoustic signalling apparatus, to be used with an implantable device having an energy source, for transmitting acoustic signals audible to the unaided ear outside the body in which the device is implanted, comprising:
 (a) a transducer for generating acoustic signals in response to applied electrical signals;
 (b) oscillator circuit means operable when energized to apply electrical signals to said transducer;
 (c) energy storage means connected to said oscillator circuit means, for providing energy to be used for energizing said oscillator circuit means, said energy storage means holding a relatively minute quantity of energy when fully charged as compared to said energy source;
 (d) switching means for selectively applying energy from the energy source to charge said energy storage means; and
 (e) means responsive to sensed conditions of the device for activating said switching means to recurrently charge said energy storage means so that between charges said energy storage means delivers a decaying pulse of energy to said oscillator circuit means which in turn applies said electrical signals to said transducer to cause said transducer to emit corresponding pulses of acoustic energy audible outside the body by the unaided ear, said pulses having a duration corresponding to the discharge period of said energy storage means and having an acoustic energy limited by the energy available from said energy storage means wherein relatively smaller quantities of power are utilized to signal as compared to energizing said oscillator circuit means and transducer directly from said energy source.

13. Low power consumption pulsed acoustic signalling apparatus, to be used with an implantable device having an energy source and a housing, for transmitting acoustic signals audible to the unaided ear outside the body in which the device is implanted, comprising:
 (a) a piezoelectric element, having a pair of electrodes for energization thereof and a feedback electrode, for generating acoustic signals in response to applied electrical signals;
 (b) means for mounting said piezoelectric element to the housing of said implantable device;
 (c) oscillator circuit means operatively connected to said energization electrodes and said feedback electrode and operable when energized to apply electrical signals to said piezoelectric element, said oscillator circuit means including means for controlling the frequency of said electrical signals in response to the feedback from said piezoelectric element to said oscillator;
 (d) energy storage means connected to said oscillator circuit means for energization thereof; and
 (e) means responsive to sensed conditions within the body and operatively connected for recurrently applying discrete quantities of energy to said energy storage means from the energy source within the implantable device for causing said piezoelectric element to emit corresponding pulses of acoustic energy audible outside the body by the unaided ear.

14. Low power consumption pulsed acoustic signalling apparatus, to be used with an implantable device having an energy source and a housing, for transmitting acoustic signals audible to the unaided ear outside the body in which the device is implanted, comprising:
 (a) a piezoelectric element, having a pair of electrodes for energization thereof and a feedback electrode, for generating acoustic signals in response to applied electrical signals;
 (b) means for mounting said piezoelectric element to the housing of said implantable device;
 (c) oscillator circuit means operatively connected to said energization electrodes and said feedback electrode and operable when energized to apply electrical signals to said piezoelectric element, said oscillator circuit means including means for controlling the frequency of said electrical signals in response to the feedback from said piezoelectric element to said oscillator;
 (d) energy storage means connected to said oscillator circuit means for energization thereof; and
 (e) means responsive to sensed conditions of the device and operatively connected for recurrently applying discrete quantities of energy to said energy storage means from the energy source within the implantable device for causing said piezoelectric element to emit corresponding pulses of acoustic energy audible outside the body by the unaided ear.

* * * * *

UNITED STATES PATENT AND TRADEMARK OFFICE
CERTIFICATE OF CORRECTION

PATENT NO. : 4,481,950

DATED : November 13, 1984

INVENTOR(S) : Stephen R. Duggan

It is certified that error appears in the above-identified patent and that said Letters Patent is hereby corrected as shown below:

Column 1, line 25
  "measuirg" should be --measuring--

Column 1, line 59
  "abovementioned" should be --above-mentioned--

Column 10, line 14
  "10" should be --2--

Column 10, line 66
  "emergization" should be --energization--

Signed and Sealed this

Seventeenth Day of December 1985

[SEAL]

Attest:

DONALD J. QUIGG

Attesting Officer

Commissioner of Patents and Trademarks